United States Patent
Morales

(10) Patent No.: US 10,500,291 B2
(45) Date of Patent: Dec. 10, 2019

(54) MECHANISMS INVOLVED IN THE FORMATION OF BIOCOMPATIBLE LIPID POLYMERIC PATCHY PARTICLES

(71) Applicant: GEORGE MASON UNIVERSITY, Fairfax, VA (US)

(72) Inventor: Carolina Salvador Morales, Arlington, VA (US)

(73) Assignee: George Mason University, Fairfax, VA (US)

( * ) Notice: Subject to any disclaimer, the term of this patent is extended or adjusted under 35 U.S.C. 154(b) by 177 days.

(21) Appl. No.: 15/055,142

(22) Filed: Feb. 26, 2016

(65) Prior Publication Data

US 2016/0250357 A1 Sep. 1, 2016

Related U.S. Application Data

(60) Provisional application No. 62/120,984, filed on Feb. 26, 2015.

(51) Int. Cl.
*A61K 49/22* (2006.01)

(52) U.S. Cl.
CPC .......... *A61K 49/225* (2013.01); *A61K 49/223* (2013.01)

(58) Field of Classification Search
None
See application file for complete search history.

(56) References Cited

U.S. PATENT DOCUMENTS

| | | | |
|---|---|---|---|
| 9,333,163 B2 * | 5/2016 | Farokhzad | A61K 8/14 |
| 2007/0014752 A1 * | 1/2007 | Roy | C08J 3/128 |
| | | | 424/78.08 |
| 2013/0064776 A1 * | 3/2013 | El Harrak | G01N 33/54346 |
| | | | 424/9.6 |

OTHER PUBLICATIONS

Raichur et al (Hollow polymeric (PLGA) nano capsules synthesized using solvent emulsion evaporation method for enhanced drug encapsulation and release efficiency. Materials Research Express. 1; (2014) p. 1-15) (Year: 2014).*

Yoon et al (Nanoparticles of Conjugated Polymers Prepared from Phase-Separated Films of Phospholipids and Polymers for Biomedical Applications. Adv. Mater. 2014, 26, 4559-4564). (Year: 2014).*

* cited by examiner

*Primary Examiner* — Jake M Vu

(74) *Attorney, Agent, or Firm* — Ballard Spahr LLP

(57) ABSTRACT

The invention relates to lipid polymeric patchy particles formed by nanoprecipitation and emulsification processes, utilizing a polymer blend including the polymer, solvent and lipid-PEGylated functional groups. More particularly, the invention relates to synthesizing particles having different or pre-selected morphologies (internal and external) and physicochemical properties. It has been found that the shear stress experienced by the polymer blend during emulsification can impart certain external and internal morphology and physicochemical properties to the resulting particles. Further, the one or more patches of the particles can be functionalized, such as, with gold nanoparticles, for use of the particles, in particular, in photoacoustic and ultrasound imaging.

13 Claims, 4 Drawing Sheets

MECHANISMS INVOLVED IN THE FORMATION OF BIOCOMPATIBLE LIPID POLYMERIC PATCHY PARTICLES

CROSS-REFERENCE TO RELATED APPLICATIONS

This application claims priority under 35 U.S.C. § 119(e) to U.S. Provisional Patent Application Ser. No. 62/120,984, filed Feb. 26, 2015, entitled "Mechanisms Involved in the Formation of Biocompatible Lipid Polymeric Patchy Particles", which is herein incorporated by reference.

GOVERNMENT SUPPORT

This invention was made with government support under Grant No. CBET-1348112 awarded by the National Science Foundation (NSF). The government has certain rights in the invention.

FIELD OF THE INVENTION

The invention relates to lipid polymeric patchy particles and syntheses for their preparation. More particularly, the invention relates to methods of controlling or tuning physicochemical properties and, the external and internal morphology, of the patchy particles.

BACKGROUND OF THE INVENTION

Patchy particles are a class of anisotropic particles that are characterized by having one or more surface-exposed domains with different surface chemistry relative to the rest of the particle. The anisotropic feature of nano- and micron-size patchy particles can be created using several techniques including template-assisted fabrication, electrified jetting, glancing angle deposition, lithography, and phase segregation. The anisotropic feature is advantageous because it allows fabrication of systems at nano- and micron-scale sizes that can perform multiple functions. The patchy polymeric particles provide the ability to simultaneously present two different surface chemistries on the same particle. There are diverse medical and industrial applications that may benefit from the use of patchy-lipid polymer particles including vaccines, drug delivery, sensors, photonics, imaging, tissue engineering and environment chemistry.

There is a need in medicine for the development of theranostic devices, which are systems that perform at the same time therapeutic and imaging functions. In cancer, theranostic devices are needed because they can be used to distribute a drug homogenously in the tumor vasculature by assistance of an imaging function. In this way, the multi-drug resistance phenomenon, which is often observed in cancer, may be significantly diminished. In tissue engineering, a patchy surface can uniquely advance medicine as it allows functionalizing the patches with multiple ligands to target different types of cells. In biomedical imaging, the patch cluster effect can significantly enhance the imaging signal due to the high density of imaging molecules in a well-defined region of the carrier.

Methods are known in the art for synthesizing patchy particles. For example, the synthesis of lipid polymeric patchy particles is described in "Spontaneous Formation of Heterogeneous Patches on Polymer-Lipid Core-shell Particle Surfaces during Self-Assembly", Small, 2012. The particles can be synthesized using nanoprecipitation and emulsion methods.

Particle formation depends on physical and mechanical parameters. The shear stress that a polymer blend undergoes during the emulsification step in the particle's synthesis has been found to be an important parameter for the formation of particles with patches. Thus, it is desirable to evaluate the role of the shear stress in the formation of the internal and external morphology of lipid polymeric patchy particles with single and multiple patches.

SUMMARY OF THE INVENTION

In one aspect, the invention provides a lipid polymeric patchy particle that includes a hollow core, a shell surrounding the hollow core and, a single patch formed on the particle's shell; or a solid core, a shell surrounding the solid core, and multiple patches formed on the particle's shell.

At least one of the core and the shell can have formed thereon lipid structures different from the one or more patches.

In certain embodiments, the lipid polymeric patchy particle includes one or more biocompatible, biodegradable polymers. The one or more polymers can be selected from the group consisting of sodium polystyrene sulfonate, polyethers, such as polyethylene oxide, polyoxyethylene glycol and/or polyethylene glycol, polyethylene imine, a biodegradable polymer such as polylactic acid, polycaprolactone, polyglycolic acid, poly(lactide-co-glycolide) polymer (PLGA), and copolymers, derivatives and mixtures thereof. A preferred polymer is PLGA. Further, the lipid polymeric patchy particle can include a semi-conductor polymer, such as, poly [2,6-(4,4-bis-(2-ethylhexyl)-4H-cyclopenta[2,1-b;3,4-alt-4,7(2,1,3benzothiadiazole)] (PCP-DTBT), which can form an inner lining in the particle core of particles with a hollow core or can be embedded in particles with a solid core.

The lipid polymeric patchy particle can include one or more lipid-PEGylated-functional groups. For example, DSPE-PEG-R, wherein R is amino, methoxyl or maleimide.

The shell can include a first shell and a second shell. The first shell can be formed by one type of LPFG (e.g., DSPE-PEG-NH$_2$) and the second shell can be formed by a different LPFG (e.g., DSPE-PEG-maleimide).

The hollow core can include at least one payloads, such as, a drug, a fluorescent dye and mixtures and combinations thereof.

In another aspect, the invention provides a method of synthesizing a lipid polymeric patchy particle having a single patch or multiple patches. The method includes dissolving the polymer in a first solvent forming a first solution (often referred to as an oil phase); dissolving lipid-PEGylated-functional groups in a second solvent (such as, water or a mixture of water and ethanol) forming a second solution (often referred to as an aqueous phase); the first and second solutions forming a polymer blend; emulsifying the polymer blend using a high shear mixer assembly forming an emulsified blend; and evaporating the first and second solvents.

The first and second solvents can be different.

The particle can have a hollow core.

The external and internal morphology of the particle can be controlled by adjusting the magnitude of shear stress during the emulsification step.

High shear stress produces particles having a hollow core and a single patch.

Low shear stress produces particles having a solid core and multiple patches.

The high shear mixer assembly can include a homogenizer workhead and a rotor, and the magnitude of the shear stress can depend on size of a gap between an inner diameter of the homogenizer workhead and the outer edge of the rotor. The gap can be from about 0.100 mm to about 0.127 mm.

The method can further include functionalizing the single patch or the multiple patches with a wide variety of organic and inorganic nanoparticles, such as, proteins and gold nanorods, respectively, to form a functionalized particle. The functionalized particle with gold nanorods can be employed in photoacoustic imaging.

DETAILED DESCRIPTION OF PREFERRED EMBODIMENTS

Figure 1:
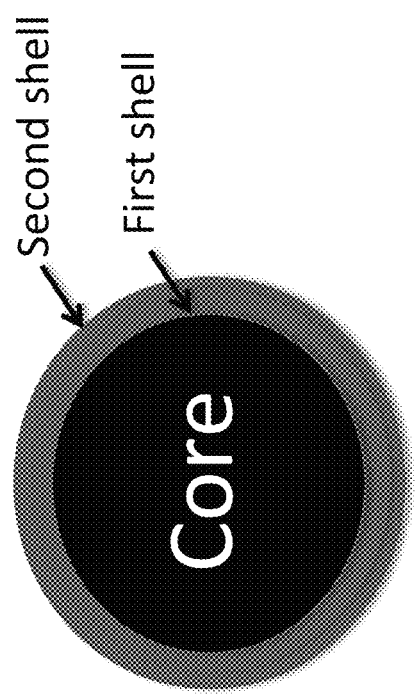
FIG. 1 is an image that shows a lipid polymeric patchy particle having a core and a double shell.

The invention relates to lipid polymeric patchy particles and, more particularly, to producing the particles having certain, e.g., pre-selected, physicochemical properties, external and internal morphologies and internal properties. Patchy particles with single and multiple patches are natural photoacoustic and ultrasound agents. The invention also relates to methods and syntheses for producing the lipid polymeric patchy particles, and mechanisms for controlling or tuning the physicochemical properties, external and internal morphology and internal properties of the particles. The particles can have one or more functionalized domains or patches that provide controllable particle binding and orientation. Further, the size of the particles, number of patches and shells, as well as the thickness of the particle's shell can be controlled or tuned in accordance with the invention. The external and internal morphology and physicochemical properties of the particles depend on chemical, physical and thermodynamic factors. For example, the chemical factors can include the solvent-solvent, polymer-solvent and polymer-polymer-solvent interactions.

Among physical or mechanical parameters, it has been found that high shear stress is the most important parameter for the formation of patchy particles. In these circumstances, the shear stress overcomes the chemical molecular forces that drive the interaction between polymer, e.g., PLGA, lipid functional group(s), e.g., DSPE-PEG-R, and solvent. The patch(es) are formed instantaneously during an emulsification step in the synthesis of the particles. The form of the patch depends on the magnitude of shear stress experienced by the polymer blend during the emulsification step. The magnitude of shear stress can vary. For example, a homogenizer's workhead with a 1" diameter used in the emulsification step of the particle's synthesis at 4000 rpm renders patch(es) that are more bulky, e.g., the patch(es) protrude or appear to "stick on" to the particle's shell. A homogenizer's workhead with a ⅝" diameter used at 4000 rm renders patch(es) that are not bulky, but rather part of the patch is embedded in the polymer matrix.

The lipid polymeric patchy particles (e.g., nanoparticles or microparticles) generally have a core-shell structure, which has a central core surrounded, or encapsulated, by a shell that forms an outer surface. In certain embodiments, the particle can have more than one shell. The one or more shells can include a single lipid-containing patch or multiple lipid-containing patches. Moreover, the lipid PEGylated functional group can form bilayers as shown by Molecular Dynamics Simulations. A single patch or multiple patches can be formed by lipid functional groups, e.g., LPFGs, on the particle's shell(s). The functional groups may be arranged in one or more of the particle's surface domains, e.g., patches, and shells, with each domain including a majority of the same type of functional group. The functional groups provide surface chemistry and surface physicochemical properties.

The core can be hollow or solid. The hollow core can be filled with one or more components, e.g., one or more "payloads", and can have a semiconducting polymer forming an inner lining in the particle's core. The solid core can have several components, e.g., "payload", embedded therein. Particles with a solid core and multiple patches can have lipid-based structures entrapped in the particle's core and on the surface. These lipid-based structures can function as enhancer contrast agents. In certain embodiments, the payload is a drug, a fluorescent dye or a mixture or combination thereof.

The particles can be loaded with a wide variety of active agents, e.g., therapeutic agents, for enhanced drug targeting and delivery, and or enhanced efficacy of the active ingredient. Thus, the particles are capable of delivering active ingredients or biofunctional agents to one or more different targets within a specific environment, e.g., the body of a human or animal subject, the skin, other organs (e.g., eye, heart, liver, pancreas, lungs and prostate).

The size of the particles can be between about 200 nm to about 10 um. In certain embodiments, patchy nanoparticles of about 200 nm size are synthesized by a mixture of DSPE-PEG-R and sodium dodecyl sulfate (SDS) at a concentration $8 \times 10^{-3}$ M. SDS reduces the particle's size and improves solubility. Nano-scale particles are generally considered to be up to 1000 nm at their largest cross-sectional dimension. Micron-scale particles are over 1.0 micron at their largest cross-sectional dimension (e.g., 1.0 micron up to 100 microns, or larger, e.g., 1.0 to 2.0 microns, 1.0 to 10.0 microns, 5 to 25 microns, and 25 to 50 microns).

The patchy particles can be formed using various polymers known in the art. Preferred polymers are biocompatible, biodegradable and FDA approved. These particles possess good blood biocompatibility properties. Generally, the particle design allows for functionalizing the surface of polymeric particles, including lipid polymeric hybrid particles, PLGA, PLA and the like, with one or more different functional groups. This design enables the particles to bind to various combinations of different biomolecules, e.g., antibodies, proteins, peptides, aptamers, and the like.

In certain embodiments semi-conducting polymer can be used to form the polymeric particles. This semiconducting polymer forms the inner lining of the particle's shell.

At least one phase can be designed to have one or more of the following properties based on the material selection: hydrophobic, positively-charged (cationic), negatively charged (anionic), and polyethylene glycol (PEG)ylated.

In certain embodiments, the particles can be formed from two elements: (i) hydrophobic polymer, which forms the hydrophobic core that may encapsulate a payload, and (ii) lipid functional group(s), which form one or more patches on the particle's core and/or shell. One end of the lipid binds to the shell of the core structure (and can extend outwards from the core shell) and another opposite end includes the functional group(s). The particles can include more than one lipid functional group. For example, a first end of a first lipid can bind to the shell of the core structure and a second end includes a first functional group, and a first end of a second lipid can bind to the shell of the core structure and a second end includes a second functional group.

Suitable non-limiting polymers for use in the invention include sodium polystyrene sulfonate, polyethers, such as polyethylene oxide, polyoxyethylene glycol and/or polyethylene glycol, polyethylene imine, a biodegradable polymer such as polylactic acid, polycaprolactone, polyglycolic acid, poly(lactide-co-glycolide) polymer (PLGA), and copolymers, derivatives and mixtures thereof.

A hydrophobic polymer for use in the invention can be selected from those known in the art, such as, but not limited to, poly(D,L-lactide-co-glycolide) (PLGA). The lipid functional group(s) also can be selected from those known in the art, such as, lipid-PEGylated-functional groups (LPFGs). The LPFGs can include a lipid bound to polyethylene glycol (PEG) and a functional group bound to the PEG. Non-limiting examples of LPFGs include, but are not limited to, 1,2-distearoyl-sn-glycerol-3-phosphoethanolamine (DSPE)-N-poly(ethylene glycol) (PEG) with a terminal or functional group R: DSPE-PEG-R, where R is amino, methoxyl, or maleimide, e.g., DSPE-PEG-NH$_2$, DSPE-PEG-OCH$_3$ and DSPE-PEG-MAL.

LPFGs can be used as building blocks for the synthesis of a wide variety of materials, e.g., nanotherapeutics, because their end-terminal functional groups can be functionalized with a variety of organic and/or inorganic molecules. Furthermore, LPFGs offer the advantage of synthesizing multifunctional nanoparticles in which high control over the number and ratio of functionalities on the particles' surface can be achieved without the need of orthogonal chemical reactions.

The LPFGs can have a different arrangement in the particle's surface as compared to the edge and center of the patch. For example, the functional group of the DSPE-PEG-R molecule may stick out at the edge of the patch and shell, which allows functionalization with molecules, and the LPFGs in the center of the patch may have a different arrangement. For example, the DSPE fragment of the DSPE-PEG-R may be exposed to further functionalization instead of having R attached thereto.

The formation of the patches on the particles resembles the phase segregation phenomenon observed in polymer blends and lipid rafts. However, the polymer blend systems of the invention involve two different polymers, e.g., PLGA and LPFG(s), and a tri-solvent composition, e.g., water, ethanol and ethyl acetate. Therefore, without being bound by any particular theory, it is believed that the formation of patchy polymeric particles is due to the shear stress that the polymer blend undergoes during the emulsification step.

In certain embodiments, two different LPFGs are employed to produce particles having a double shell. Each of the shells having a different surface chemistry. FIG. 1 shows a particle having a core, a first shell (e.g., including a first LPFG) and a second shell (i.e., including a different second LPFG). The first shell can be formed by one type of LPFG (e.g., DSPE-PEG-NH$_2$) and the second shell can be formed by a different LPFG (e.g., DSPE-PEG-maleimide).

In certain embodiments, good blood biocompatibility is achieved using a specific LPFG, such as, DSPE-PEG-OCH$_3$, to synthesize patchy polymeric particles that likely can remain in circulation in a patient for at least 48 hours, which extends the time available for medical imaging. It has been found that patchy polymeric particles synthesized with DSPE-PEG-folic acid and a mixture of DSPE-PEG-NH$_2$ and SDS at $8 \times 10^{-3}$ M can remain in circulation for 24 hours in mice.

Lipid polymeric patchy particles can be prepared in general using various known methods. For example, single-step nanoprecipitation methods are described in U.S. Pat. No. 5,118,528, which is incorporated herein by reference. These methods can be used to synthesize nanoparticles by mixing a solution containing a substance into another solution (i.e., a non-solvent) in which the substance has poor solubility. For example, polymer (e.g., PLGA-PEG) nanoparticles can be made in which polymer solutions in either water-immiscible or water-miscible solvents are added to an aqueous fluid (i.e., the non-solvent). Such nanoprecipitation methods are also described, for example, in PCT WO 2007/150030.

Further, various methods are known to link or bind the lipid functional group(s) to the core structure using covalent bonds or non-covalent bonds, such as, Van der Waals forces, to form the particles.

Polymeric- and lipid-containing particles can be made by (i) dissolving a polymer in a volatile, water-miscible organic solvent to form a first solution (referred to as the oil phase); (ii) dissolving a plurality of first and second amphiphilic components bound to heterofunctional linkers in an aqueous solvent to form a second solution (referred to as the aqueous phase), wherein the amphiphilic components each have a hydrophobic end and a hydrophilic end, the first heterofunctional linker each includes a first functional group, and the second heterofunctional linker each includes a second functional group, and (iii) combining the first and second solutions such that a polymeric nanoparticle is formed having a polymer core surrounded by amphiphilic components, wherein the heterofunctional linkers extend from the amphiphilic components and the first and second functional groups form an external mosaic of surface domains, each domain generally including a majority of one type of functional group.

In certain embodiments, synthesis of the patchy particles includes nanoprecipitation and emulsification. Polymer and lipid solutions are mixed to form a polymer blend, which is subjected to high shear mixing to form an emulsified mixture. For example, an aqueous phase can be prepared by dissolving DSPE-PEG-R, e.g., DSPE-PEG-(2000)amine 1,2-distearoyl-sn-glycero-3-phosphoethanolamine-N-[amino(polyethylene glycol)-2000 (DSPE-PEG-NH$_2$) or DSPE-PEG(2000) maleimide 1,2-distearoyl-sn-glycero-3-phosphoethanolamine-N-[maleimide(polyethylene glycol)-2000 (DSPE-PEG-MAL) in solvent, e.g., ethanol and/or water. This solution is homogenized at, for example, 1000 rpm, for a period of time, e.g., 15 seconds. Polymer, e.g., PLGA solution (in ethyl acetate), is added to the aqueous phase. The polymer blend is homogenized, for example, at 2000 rpm or 4000 rpm or 8000 rpm for a period of time, e.g., 1 minute, using a high shear mixer and tubular mixing assembly, to produce an emulsified mixture. The solvent is then allowed to evaporate and particles are formed.

It has been found that shear stress is a critical physical factor in synthesizing the patchy particles having different internal and external morphologies. The morphology of the core and the shell can depend on the shear stress applied to the polymer blend during synthesis of the particles. Shear stress promotes and enhances mutual miscibility between PLGA and LPFGs. A sufficient magnitude of shear stress is necessary to form patchy particles; that is, without enough shear stress, patchy particles cannot be formed. Further, the shear stress can be adjusted during synthesis to impart certain morphologies to the resulting particles. The magnitude of shear stress exerted by the high shear mixer and tubular mixing assembly on the polymer solution during emulsification can impart different external and internal morphology to the resultant particles.

Without intending to be bound by any particular theory, it is believed that during the pre-emulsification step, the LPFGs form liposomes (e.g., multilamellar and unilamellar vesicles) because the concentration of LPFGs used in the particle's synthesis is above the critical micelle concentration of DSPE-PEGm. However, because of the incorporation of additional ethanol, ethyl acetate and PLGA, the physical integrity of the liposomes is affected. When previously dissolved PLGA in ethyl acetate is incorporated into the aqueous phase, a phase segregation phenomenon takes place initiated by the solvents (e.g., water-ethanol and ethyl acetate). The DSPE fragment of LPFGs interacts favorably and rapidly with the PLGA during the pre-emulsification step. The polymer blend undergoes a high shear stress during the emulsification step, which promotes the miscibility between PLGA and LPFGs giving rise to a droplet with a core-shell structure. The presence of high shear stress enhances the miscibility of the polymer blend inducing a pronounced phase segregation phenomenon that results in the formation of the core-shell structure followed by the formation of a patch. During these chemical and physical conditions, droplets coated with LPFGs having an indentation are formed, and the remaining LPFGs start forming the patch. The patch may be formed by a pile-up of lipid-based structures. The patchy particles that result from this process have a hollow core, a shell formed by PLGA-DSPE-PEG-$NH_2$, and a patch formed by a pile-up of LPFGs.

High shear stress of the polymer-lipid blend during synthesis of the particles, forms particles having a hollow core and a single lipid-containing patch. In contrast, low shear stress of the polymer-lipid blend during synthesis of the particles, forms particles having a solid core and multiple lipid-containing patches. Further, the thickness of the particle's shell can be controlled by tuning the shear stress that the polymer blend undergoes during the emulsification step of the particle's synthesis. In general, the higher the shear stress, the thicker the particle's shell. The thickness of the particle's shell can be determined by cross-sectioning particles that have core-shell and patch-core-shell structures.

Shear stress can depend on various factors, such as, the viscosity of the polymer blend solution and/or the dimension, e.g., diameter, and shape of the homogenizer workhead that is used to emulsify the polymer blend solution. The fluid mechanics as well as the fluid dynamics of the polymer solution has an influence in the shear stress that the polymer blend undergoes during emulsification.

As aforementioned, a high shear mixer and tubular mixing assembly can be used to form an emulsified mixture from the polymer blend solution. This assembly includes a homogenizer having a workhead and a rotor-shaft. Various homogenizers and workhead designs are known in the art and may be employed in the invention. In general, the homogenizer workhead is a tubular structure including a hollow space or cavity formed by a wall having an inner diameter, an outer diameter. A plurality of shaped holes are formed in the perimeter of the wall of the tubular structure, e.g., a screen, through which the polymer blend passes. The tubular structure is typically composed of metal and the holes can be round or square, and the size, e.g., diameter, of the holes can vary. In certain embodiments, the homogenizer workhead can include round holes. Further, the homogenizer workhead includes a rotor-shaft, e.g., blade, positioned within the hollow space of the tubular structure. In general, the homogenizer workhead with the rotor therein, is inserted into a container, e.g., beaker, holding the polymer blend. The polymer blend is forced into, e.g., enters, the cavity of the workhead with rotor therein, and the polymer blend is discharged through the holes, e.g., screen.

Figure 2:
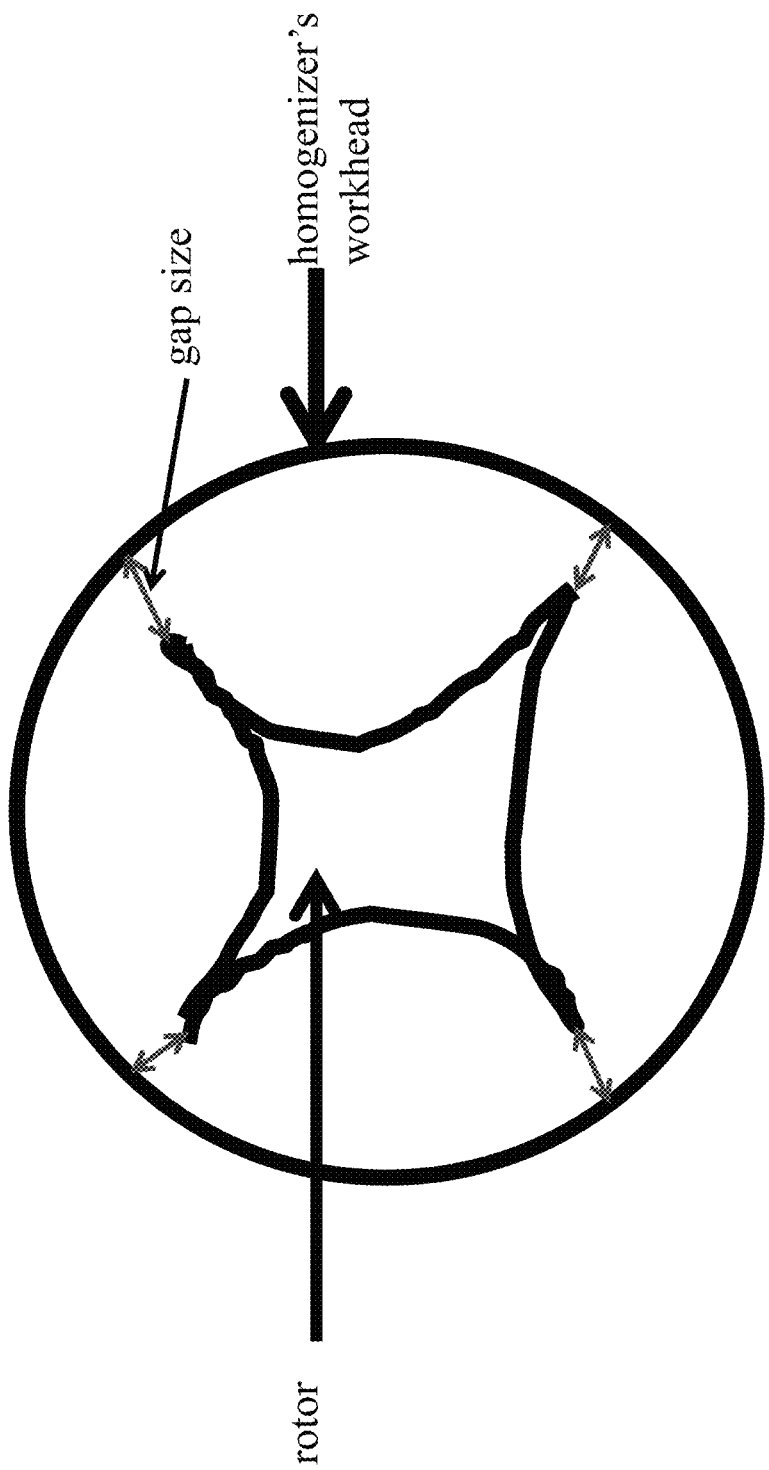
FIG. 2 is a schematic showing a top view of a homogenizer's workhead and rotor of a high shear mixer and a tubular mixing assembly.

FIG. 2 is a schematic showing an upper view of a homogenizer workhead having a rotor positioned therein. As shown in FIG. 2, there is a gap formed between the outer ends, e.g., outer edge(s), of the rotor and the inner surface or diameter of the homogenizer workhead, such that the outer ends of the rotor are not in contact with the inner surface or diameter of the homogenizer workhead. The magnitude of the shear stress is determined by the size of the gap. The smaller the gap (the shorter the distance between the outer ends of the rotor and the inner surface or diameter of the homogenizer workhead), the higher the shear stress that the polymer blend solution undergoes during emulsification in the particle's synthesis. In certain embodiments, the gap can be from about 0.100 mm to about 0.127 mm or from about 0.100 mm to about 0.137 mm. It has been determined that a gap of 0.137 mm corresponds to a shear stress of about 450 to 600 dynes/$cm^2$.

Shear stress can be calculated based on the following formula:

$$\tau = -V_t \mu \frac{2}{d}$$

wherein,
$\tau$=shear stress;
$V_t$=tangential velocity;
$\mu$=viscosity of the polymer blend solution;
d=gap size (distance or difference between the inner diameter of the homogenizer's workhead and the outer end(s)/edge(s) of the rotor); and
$V_t = \omega r$
wherein,
$\omega = 2\pi f$;
f=frequency=shear rate=revolution per minute;
$\pi$=3.1616; and
r=homogenizer's workhead radius.

High shear stress during emulsification of the polymer blend forms particles with a single patch and a hollow core because the shear stress force overcomes the van der Waals interaction between DSPE-PEG-R and PLGA. The patchy particles resulting from high shear emulsification have a hollow core, a shell formed, for example, by PLGA-DSPE-PEG-R, and a single patch formed by a pile-up of LPFGs. In contrast, low shear stress during emulsification of the polymer blend forms particles with multiple patches and a solid core because the van der Waals interaction between DSPE-PEG-R and PLGA is strong. With low shear stress, LPFGs form a thin shell on the polymeric core. When the shear stress force is low and the van der Waals interaction between DSPE-PEG-R and PLGA is strong, lipid-based structures may be formed, e.g., entrapped or embedded, into the solid core of the particles. Without intending to be bound by any particular theory, it is believed that the lipid-based structures include a particular arrangement of lipid-polymer based functional group. The lipid-based structures may also form on the shell.

Controlling or tuning the magnitude or degree of shear stress during particle synthesis can determine the morphology of the particle, i.e., core-shell and core-shell-patch, and the thickness of the shell.

Figure 3:
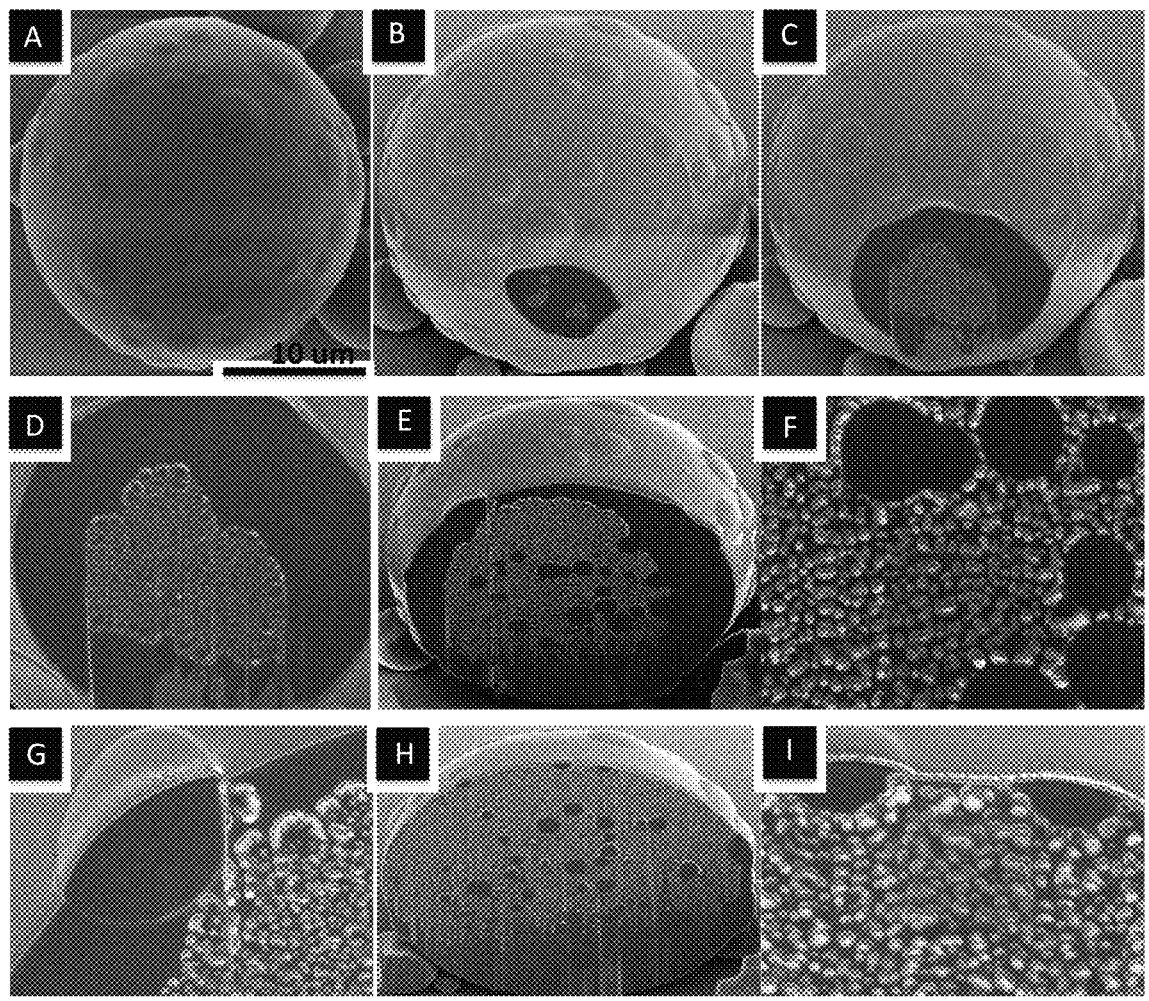
FIG. 3 includes images (Views A through I) showing the external and internal morphology of a lipid polymeric particle with multiple patches and a solid core, in accordance with certain embodiments of the invention.

FIG. 3 shows images of a lipid polymeric particle with multiple patches formed in accordance with certain embodiments of the present invention. View A is an image showing the external morphology of the particle including multiple patches, e.g., LPFGs. Views B through I are images of the internal morphology of the particle based on cross sections of the same particle at different or varying depths. View B shows a solid core and Views C-I show lipid-based structures that are formed, e.g., entrapped or embedded, in the solid core. In particular, View F is a close-up of the lipid-based structures embedded in the particle core; View G shows an arrangement of lipid-based structures near a patch; View H shows the half of the particle's core completely covered by lipid-based structures; and View I is a close-up of the lipid-based structures near a patch. Based on these images, it is evident that the lipid-based structures found in the particle's core have a different arrangement or configuration from that of LPFGs in the patch.

Figure 4:
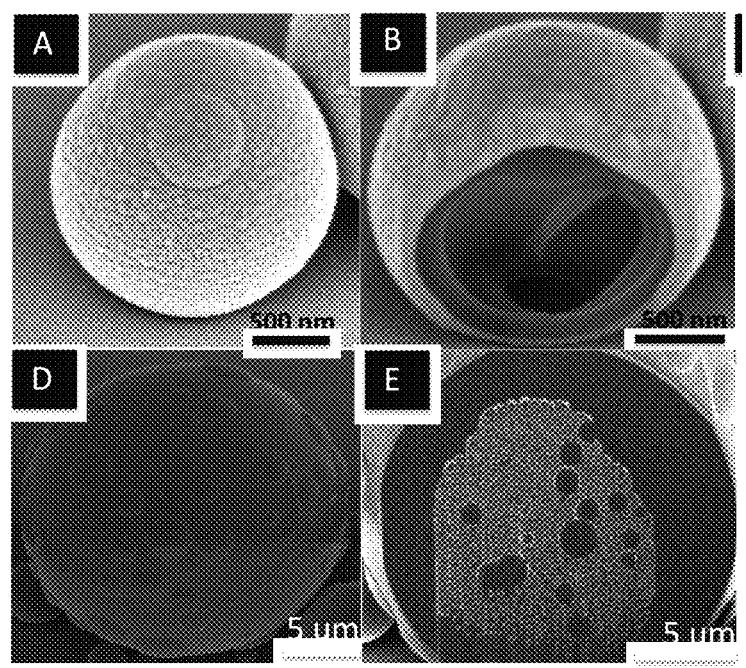
FIG. 4 includes images (Views A, B, D and E) showing the external and internal morphology of lipid polymeric particles, in accordance with certain embodiments of the invention.

FIG. 4 shows images of lipid polymeric particles with different internal and external structures. View A is an image of the external morphology of a particle having a single patch and View B is a cross-section of the internal morphology of the same particle having a hollow core. View D is an image of the external morphology of a particle having multiple patches and View E is a cross-section of the internal morphology of the same particle having a solid core and lipid-polymer-based structures entrapped in the core.

As mentioned herein, patchy particles having surface domains or patches provide advantages in a wide variety of fields and applications. Such applications include imaging applications because the clusters on the particle's surface can enhance the imaging signal. This effect will reduce toxicity and maximize the imaging effect. It was found that the absorbance of particles that have a patch-core-shell structure is 1.5 times higher than particles that have only a core-shell structure. The absorbance of particles that have two shells and two patches has three times the absorbance of core-shell structure and twice the absorbance of the single patch-core-shell structure. The higher the absorbance, the higher the amount of light absorbed by the particle. This high absorption property of these patchy particles is advantageous for photoacoustic and ultrasound imaging where the adsorbed light is converted into heat leading to a transient thermoelastic expansion and ultrasonic detection, which will form the image.

Controlling the thickness of the particle's shell is useful for photoacoustic and ultrasound applications because thin shells can be disrupted easily with light. The methods of the invention provide the capability of synthesizing patchy particles with very thin shells.

Further, semi-conductor polymer, such as, poly [2,6-(4, 4-bis-(2-ethylhexyl)-4H-cyclopenta[2,1-b;3,4-alt-4,7(2,1, 3benzothiadiazole)] (PCPDTBT), can be incorporated during synthesis, e.g., in the polymer blend. The semiconductor polymer can form an inner lining in the particle core of particles with a hollow core or can be embedded in particles with a solid core. That is, patchy particles having an inner lining are produced when the shear stress is high or patchy particles having the semiconducting polymer embedded in the polymer matrix are produced when the shear stress is low. These types of arrangements of the semiconducting polymer can be advantageous for use in medicine.

Polymeric particles with multiple patches are unique materials because their external surface is different from their internal morphology, which provides several advantages. For example, the outer surface has multiple domains that can be further functionalized with a variety of organic or inorganic molecules, e.g., nanoparticles, such as, but not limited to proteins and gold nanorods, respectively. The polymer particles functionalized with gold nanorods can be employed for imaging purposes because these particles emit a photoacoustic (PA) signal.

In certain embodiments, LPFGs form a patch on a lipid polymeric particle and a portion of the LPFGs that form the patch are functionalized with gold nanorods. The R fragment of DSPE-PEG-R protrudes, e.g., "sticks-out", such that it may be functionalized. The LPFGs that form the center of the patch may have a different arrangement from the one observed at the edge of the patch. Gold nanorods have high attenuation coefficient. The thinner the particles' shell, the less is the attenuation coefficient and the higher the adsorption and thermal expansion. Therefore, the higher is the resolution of the image obtained using the photoacoustic method.

The lipid polymer patchy particles combine characteristics of both liposomes and polymer particles, and are able to carry poorly soluble materials, e.g., drugs. Their circulation half-life is longer than that of polymeric particles, and slightly shorter than that of liposomes. These particles have multivalent targeting abilities and can be designed to provide a sustained and/or controlled drug release.

Furthermore, the patchy particles can encapsulate a wide range of pesticides, such as atrazine, which is the most widely used herbicide in the market. Also, at the same time, through the patch there can be released growth factor that can promote and enhance the growth of the plant. Particles with multiple patches can be used as carriers for multiple-growth factor clusters. Particles with two patches and two shells can release a pesticide through the core and release two different growth factors through the heterogeneous patches and shells.

It will be appreciated by those skilled in the art that changes could be made to the embodiments described above without departing from the broad inventive concept thereof. It is understood, therefore, that this invention is not limited to the particular embodiments disclosed and the following examples conducted, but it is intended to cover modifications that are within the spirit and scope of the invention.

EXAMPLES

Solvents used in the examples were purchased at analytical grade from Sigma-Aldrich (St. Louis, Mo.). DSPE and PEG-based polymers were purchased from Avanti Polar Lipids (Alabaster, Ala.) and Laysan Bio (Arab, Ala.). PLGA was purchased from Lactel (Pelham, Ala.).

Example 1—Patchy Particle's Internal Structure

To further understand the role of the shear stress in patchy particle formation, particles at different shear stress rates were synthesized. It was found that multiple and single patches were formed at 2000 rpm and 4000 rpm, respectively. Previously, by cross sectioning the single-patch particles, it was found that these particles have a hollow core.

Using the same rationale, a cross-section was taken of the particles with multiple patches. The cross-sections revealed that these particles had a solid core with entrapped lipid-based structures. Upon cross-sectioning of the particle's core, it was observed that the lipid-based structures were embedded in the entire polymer matrix. Moreover, the lipid-based structures were only observed in the particle's core and not in the patch or patches. This finding suggested that although the lipid-based structures in the particles' core were made of LPFG, their arrangement was different from that in patch or patches. In fact, the lipid-based structures in the particle's core tended to separate from the patch or patches.

Computational Fluid Dynamic (CFD) simulations showed that the wall shear stress at 2000 rpm was very low compared with that at 4000 rpm. Based on these results, it was evident that the shear stress rate is determinative of whether a particle's internal structure is solid or hollow.

Molecular Dynamics (MD) simulations were developed to evaluate the self-assembly process of PLGA and LPFG. Due to the high number of atoms needed to develop a MD of a microparticle of an average size of 2 μm in diameter, it was necessary to perform MD of a nanoparticle of 18 nm in diameter. This nanoparticle was made of poly (lactic-co-glycolic acid (PLGA)), a biocompatible, biodegradable and FDA-approved polymer. The two monomers of PLGA: lactic acid and glycolic acid were built and later replicated at random, making a total of 419 lactic acid (76%) and 131 glycolic acid (24%) monomers for a single chain of PLGA.

Full atomistic MD simulation was carried out to elucidate the nature of the interactions that drive the formation of DSPE-PEG-NH$_2$/PLGA complex. To achieve this goal, pair interaction energy values were obtained from DSPE (tails)-PLGA, PEG-PLGA and PEG-DSPE (tails) fragments, of the same number of atoms, taking into account the last part of the simulation. This calculation was performed using NAMD Energy plugin included in VIVID software. As hypothesized, the van der Waals energy between the polymers was more relevant than the electrostatic energy. MD revealed that the most favorable van der Waals interaction occurred between DSPE and PLGA as the interaction between the DSPE and PEG sections was displaced. The DSPE-PEG interaction was more relevant at the beginning of MD but that interaction changed as time passed. Similarly, PEG and PLGA also showed a favorable van der Waals interaction but not as strong as DSPE-PEG. Furthermore, as was observed from a radial distribution function (RDF), DSPE tails were partially embedded into PLGA nanoparticle, while some sections were interacting with PEG polymers. PEG section was also in part buried into PLGA. DSPE appeared as an interface between PEG and PLGA, while PEG tended to displace more towards the surface. At the same time, the calculation of solvent accessible surface area (SASA) ratified that DSPE-PEG remained more protected from the environment (lower values of SASA) being in contact with PLGA polymers. It was evident how PLGA and DSPE-PEG-NH$_2$ interacted to each other between the hydrophobic regions. Knowing the interaction between PLGA and DSPE-PEG-R contributes to acquiring more control on the particle's surface chemistry, and therefore assists in improving their clinical performance, as the particle's surface chemistry plays an important role in the protein-corona effect. Moreover, use of the MD simulations can vary the PEG's molecular weight and molar ratio with respect to the PLGA to predict the particle's surface chemistry.

Coarse-grained MD were developed to understand the formation of the hollow aspect of the particle's core. In this type of simulation, a variable pressure was incorporated to emulate the shear stress that the polymer blend undergoes during the emulsification step of the particle's synthesis. To start the simulation, DSPE-PEG polymers were placed at random, in a water box, on the top of the PLGA nanoparticle (FIG. 3*bia*). As the simulation continued, hydrophobic DSPE tails started to agglomerate, while water penetrated both PEG sections and PLGA block. Towards the end of the simulation, there was observed the formation of bilayers which were composed by DSPE molecules, while DSPE-PEG polymers collapsed into the surface of the PLGA nanoparticle due to the effects of the high pressure applied to the system. Analysis of the system density over the last frame of the simulation showed that PLGA density encompassed the area 0 nm<z<15 nm. The density of the nanoparticle did not constitute a rigid core. Specifically, the area where the density decayed (3 and 8 nm in the z-axis) coincided with an increase in the density of water in that zone. Moreover the fact that the density of water is >0 along the block demonstrated that water can penetrate PLGA and PEG sections. As a result of this phenomenon, the nanoparticle formed by the PLGA polymer showed some cavities inside, denoting the entry of water. Experimentally, it was found that particles with single patches have a hollow core. Initially, it was hypothesized that the particle's hollow core was formed because the shear stress force that the polymer blend undergoes during the emulsification step in the particles synthesis, overcomes the van der Waals interaction that exists between DSPE-PEG-R and PLGA. Although the cavity of the particles was observed in MD when the nanoparticle's core was already formed, it was evident that the pressure parameter incorporated into the MDS or the shear stress force applied during the emulsion of the polymers caused the particle's hollowness.

Example 2—Particle's External Structure

MD was also employed to provide information about the arrangement of the LPFGs in the particle's surface. These MD showed that the hydrophobic tails (DSPE) distribution displayed regular peaks, indicating the formation of bilayers along the block. A single peak of DSPE was near the surface of PLGA nanoparticle (z=12), showing tails that collapse into its surface. PEG sections were distributed in the same area as DSPE, 5 nm<z<35 nm. Where the density of PEG decayed, the density of water increased, showing that this polymer was acting as a sponge. In fact, the ground section of the block, encompassing the area 0<z<13, was similar as compared with the nanoparticle formed along the full-atom molecular dynamics simulation. In this area, PEG and PLGA competed in the interaction with DSPE tails.

To facilitate the analysis of the bilayers formed during the coarse-grained simulation, there was selected a small block of DSPE-PEG polymers from the final aggregate. As was deduced from density profile, DSPE tails occupied the area 5 nm<z<11 nm. DSPE head groups (defined by -NH$_3^+$ groups) represented by two peaks (purple line), in the region 4-6 nm and 10-12 nm, denoted the interfacial area of the lipids, showing the typical profile of a bilayer. PEG polymers were distributed in the upper and lower part of the bilayer, which decreased their density in the DSPE bilayer area. A schematic representation of the arrangement of DSPE-PEG-NH$_2$ on the particle's surface was observed. MD simulations confirmed that DSPE fragment of the LPFGs formed not only the interface between PLGA and DSPE-PEG-NH$_2$ but also the formation of a bilayer in the particle's surface. Moreover, MDS showed that part of DSPE and PEG are buried in PLGA. The structural information about the arrangement of the LPFG in the particle's surface was necessary to achieve high control on patchy particles' surface chemistry. This information also may be relevant for the selection of the payloads for a particular application.

The MDs showed that some molecules of H$_2$O were also entrapped in the particle's core whether the core was solid or hollow. Because of the effect of the pressure, and due to the water being incompressible, several holes were formed in the PLGA nanoparticle. The lipid and polymer molecules offered more interstice that may experience more compression than bulk water. When the shear stress force was low, the van der Waals interaction between PLGA and DSPE-PEG-NH$_2$ was strong, leading to the formation of a solid particle's core with entrapped lipid-based structures. The lipid-based structures formed in the particle's core were presumably a particular arrangement of lipid-polymer based functional group. MD showed how the DSPE fragment of the DSPE-PEG-NH$_2$ interacted closely and preferentially with the lactic monomer, which was not unexpected because the DSPE fragment and lactic acid are hydrophobic. Moreover, in the presence of low shear stress many DSPE-PEG-NH$_2$ got entrapped in the particle's core because of the high diffusion coefficient of the DSPE fragment that enhanced and facilitated its interaction and penetration into the PLGA copolymer.

MD simulations demonstrated the formation of a lipid bilayer in the particle's shell formed by DSPE-PEG-R, which is an important finding because it provides insights about the particle's surface. Therefore, the interaction of the nanocarrier with proteins and cells could be predicted. The fact that there is a lipid-bilayer in the particle's surface allows for incorporation of hydrophobic molecules between the bilayer. Also, MD simulations corroborate the experimental finding that high shear stress produces particles with a single and hollow core.

Example 3—Biomedical Applications of Patchy Polymeric Particles

It was found that the patchy polymeric particles possess unique optical properties. They induced a significant PA signal, which was dose-dependent, in the near-infrared (NIR) region (i.e, 600-950 nm). Clinically, it was known that the NIR region (700-1100 nm) is where the influence of the main tissue absorbing components, oxy-and deoxyhemoglobin (max <600 nm) as well as water (max >1150 nm) is minimal. Therefore, this region of the spectrum was considered as the ideal optimal imaging window. Particles with multiple patches induced a higher PA signal than patchy particles with single patches. The PA signal induced by particles with multiple patches and solid core was approximately 9 times higher than the one emitted by particles with single patches and hollow core when the particle's concentration was 5 mg/ml. This phenomenon was likely due to the ability of particles with multiple patches to absorb more light than single patch-particles. From the molecular level perspective, it is believed that particles with multiple patches are better natural photoacoustic contrast agents because they can offer a larger surface area to the solvent of the self-assembly process that generate the multiple patches.

Differential Scanning calorimetry was employed to evaluate the thermal properties of these particles. Both particles exhibited a relatively similar melting point temperature. The melting temperature of patchy particles with multiple patches was 59° C. and the melting point temperature for particles with a single patch was 57° C. There were only two degrees of difference between them. Furthermore, single-patch particles had a crystallization temperature (Tc) of approximately 2.2° C. while the multiple domain patchy particles had a Tc of approximately −5° C. The one sharp peak for each sample indicated that these samples were pure. Since the peaks were not broad, both samples were not partially crystalline polymers but were amorphous. Since both samples contained no α-nuclei, they had no crystallization peak and no α-melting peak. The baseline shifted lower towards the endothermic direction after the peak for both samples due to the increased heat capacity of the sample. The most significant difference between particles with single and multiple patches was the enthalpy, the area under their peaks. Particles with multiple patches exhibited higher enthalpy than that of particles with single patches, which means that the former absorbed more heat than particles with individual patches. This thermal profile correlated well with the intrinsic photoacoustic properties of patchy particles. High enthalpy seemed to render higher photoacoustic signal. It was attempted to enhance or modulate their PA signal by functionalizing their patch or patches with exogenous PA contrast agents, such as, gold nanorods and nanoshells or by tuning their internal properties. It is known to use PLGA particles as carriers for contrast agents. The multiple patches can play an unparalleled imaging performance because of the cluster effect induced by the patch.

Results and Conclusions of Examples 1-3

There was evaluated the self-assembly process involved in the formation of PLGA particles with single and multiple patches which are formed by the unique arrangement of LPFGs. It was found that in the presence of a high shear stress force, particles with a single patch and with a hollow core are formed because the shear stress force overcomes the van der Waals interaction between DSPE-PEG-R and PLGA. Particles with multiple patches and solid core are formed when the shear stress is low, and therefore the van der Waals interaction between DSPE-PEG-R and PLGA is strong. Thus, the shear stress determines both the internal and external morphology of PLGA particles as well as their unique natural PA properties. Additionally, MD revealed the formation of a lipid bilayer on the particle's surface.

Example 4—Synthesis of Lipid Polymeric Patchy Particles

Particles with single and multiple patches were prepared by a single-emulsion method as reported in Salvador-Morales and Rasheed et al. Briefly, the aqueous phase of the mixture was prepared by dissolving DSPE-PEG(2000) amine 1,2-distearoyl-sn-glycero-3-phosphoethanolamine-N-[amino(polyethylene glycol)-2000 (DSPE-PEG-NH$_2$) or DSPE-PEG(2000) maleimide 1,2-distearoyl-sn-glycero-3-phosphoethanolamine-N-[maleimide(polyethylene glycol)-2000 (DSPE-PEG-MAL) in 4% ethanol to a concentration of 1 mg/ml. To this solution, 6 mL of 4% ethanol was added, and the solution was homogenized at 1000 rpm for 15 s. 4 mL of PLGA solution (15 mg/mL in ethyl acetate) was immediately added to the aqueous phase. The mixture was homogenized at 2000 rpm or 4000 rpm for 1 min using a L5M-A high shear mixer and ⅝ in. tubular mixing assembly. Fifty mL of deionized water was added dropwise to the emulsified mixture, and the volatile solvent was allowed to evaporate overnight. Particles were centrifuged at 2000 rpm for 10 minutes using Millipore Amicon Ultra centrifugal filter units with a MWCO of 100 kDa to remove completely the remaining solvent and washed three times with deionized water. Subsequently, particles were examined with a FE-SEM (Zeiss) operating at 1.00 kV accelerating voltage to visualize the particle's surface. The aqueous phase of particles with multiple patches was prepared with 1 ml of DSPE-PEG-NH$_2$ and 1 ml DSPE-PEG-MAL. DSPE-PEG-NH$_2$ was labeled with Alexa 594 (5 ug) before being mixed with DSPE-PEG-MAL.

Example 5—Focused-Ion Beam and Cross Sections

Patchy polymeric microparticles were cross-sectioned using a FEI Focused Ion Beam (FIB) with a gallium ion source operated at 1 kV, SE mode, and 25000× magnification. Patchy microparticles were previously coated with gold-palladium alloy to protect particles from the ion beam.

Example 6—Computational Fluid Dynamics Simulations

To demonstrate the dependence of the fluid shear stress on the size of the gap between the inner diameter of the homogenizer tubular assembly's workhead and the rotor shaft, computational fluid dynamics (CFD) simulations were carried out for a gap size of 0.137 mm. The numerical solutions of 3D incompressible Navier-Stokes equations were obtained with an edge based finite element solver. Unstructured grids composed of tetrahedral elements were generated and locally refined near the inner wall to obtain at least two points within the gap. The resulting mesh had approximately 3 million elements. The rotating piece was modeled using immersed boundary methods based on unstructured grids. The rotor shaft was set in rigid-body rotation around its axis at 4000 rpm and 2000 rpm. No slip boundary conditions were applied at all body surfaces, including the rotating rotor shaft. The polymer fluid density was set to 1.0 g/cm$^3$ and the viscosity to 0.031 dyn s/cm$^2$. The viscosity of the polymer solution was measured using a MCR702 rheometer (Anton Paar GmbH) with a double-gap configuration. An explicit three-stage Runge-Kutta scheme with CFL=0.6 and a maximum time step of $5 \times 10^{-5}$ was used to advance the flow solution. All simulations were carried out in parallel on shared memory computers using OpenMP and were run on 16 processors. Results were saved at $1.5 \times 10^{-4}$ s intervals and animations of the wall shear stress in the gap region were created.

Example 7—Hollow Patchy Polymeric Particle Synthesis

Hollow patchy polymeric particles were synthesized with different workhead dimensions including 3/8", 5/8" and 1". The 1" workhead with a square screen head produced particles with "bulky patches" (see FIG. 1EX). These particles had a hollow core and very thin shell of approximately 2 nm in thickness (see FIG. 2EX). The particles synthesized with 1" workhead were synthesized at different angular speeds (rpm) ranging from 2000 rpm to 10000 rpm. When scaling up the particle synthesis, the size of the patch of particles synthesized with 5/8", 3/8" and 1" workheads depended on the emulsification time and the angular speed. This was because a high volume of polymer solution required more "mechanical energy" to emulsify the polymer solution than that required to emulsify a low volume of polymer solution. For example, when the volume of the polymer solution was 72 ml, the largest patches were formed when the polymer solution is emulsified at 8000 rpm at 4 min using the 1" workhead. As the volume of the polymer solution was increased, the emulsification time needed to be increased.

Patchy particles synthesized with 1" and 5/8" workheads had a high optical density at different wavelengths. The optical density of these patchy particles was approximately three times higher than the optical density of gold nanorods which have been used as standard contrast agents in photoacoustics. These patchy particles displayed high optical density even at 800 and 900 nm, whereas the optical density displayed by gold nanorods is typically very low at these wavelengths. Because the absorption spectrum of these particles was high in the range of 600 to 900 nm, these particles could perform exceptionally as contrast agents for photoacoustics and ultrasound applications. In addition, patchy particles synthesized with the 1" workhead had a very thin shell, which provides the potential to break up that shell with an external stimulus, such as, a laser. This peculiar feature of these particles may be advantageous for a medical treatment wherein it is required that the drug be released completely at once. Thus, these patchy particles may be ideal carriers for a theranostic application where both imaging and therapeutic effects are provided simultaneously.

The invention claimed is:

1. A lipid polymeric patchy particle comprising:
   a hollow core having an inner lining and an outer surface surrounding the inner lining,
   one or more shells surrounding the outer surface,
   a single patch formed on the outermost shell, and
   a first lipid functional group having a first end and a second end, wherein the first end is bound to the outer surface, thereby forming a first shell, and wherein the second end has a first functional group,
   wherein the inner lining comprises a semi-conductor polymer and
   wherein the outer surface comprises a hydrophobic polymer.

2. The particle of claim 1, wherein the particle further comprises a second lipid functional group having a first end and a second end, wherein the first end of the second lipid functional group is bound to the outer surface, thereby forming the first shell, together with the first lipid functional group, and wherein the second end of the second lipid functional group has a second functional group, wherein the first lipid functional group and the second lipid functional group are different.

3. The particle of claim 1, wherein the hydrophobic polymer is a biocompatible, biodegradable polymer.

4. The particle of claim 1, wherein the hydrophobic polymer is poly(lactide-co-glycolide) polymer.

5. The particle of claim 1, wherein the first lipid functional group is a lipid-PEGylated functional group.

6. The particle of claim 5, wherein the first lipid functional group has a formula: -1,2-distearoyl-sn-glycerol-3-phosphoethanolamine (DSPE)-N-poly(ethylene glycol) (PEG)-R, wherein R is a functional group.

7. The particle of claim 5, wherein the first lipid functional group has a formula: -DSPE-PEG-R, wherein R is selected from amino, methoxyl, and maleimide (MAL).

8. The particle of claim 1, wherein the particle comprises the first shell and a second shell, wherein the second shell surrounds the first shell.

9. The particle of claim 8,
   wherein the particle further comprises a second lipid functional group having a first end and a second end, wherein the first end of the second lipid functional group is bound to the second shell and wherein the second end of the second lipid functional group has a second functional group, and wherein the first lipid functional group and the second lipid functional group are different.

10. The particle of claim 9, wherein the second lipid functional group has a formula -DSPE-PEG-$NH_2$ and wherein the different lipid functional group has a formula -DSPE-PEG-MAL.

11. The particle of claim 1, wherein bound is via covalent bonds.

12. The particle of claim 1, wherein the semi-conductor polymer is poly [2,6-(4,4-bis-(2-ethylhexyl)-4H-cyclopenta [2,1-b, 3, 4-alt-4,7(2, 1, 3-benzothiadiazole)] (PCPDTBT).

13. The particle of claim 1, wherein the hollow core contains a payload.

* * * * *